(12) United States Patent
Koehler et al.

(10) Patent No.: US 11,202,609 B2
(45) Date of Patent: Dec. 21, 2021

(54) GRID-MOUNTING DEVICE FOR SLIT-SCAN DIFFERENTIAL PHASE CONTRAST IMAGING

(71) Applicants: KONINKLIJKE PHILIPS N.V., AE Eindhoven (NL); PAUL SCHERRER INSTITUT, Villigen (CH)

(72) Inventors: Thomas Koehler, AE Eindhoven (NL); Ewald Roessl, AE Eindhoven (NL); Matthias Bartels, AE Eindhoven (NL); Zhentian Wang, Brugg (CH); Marco Stampanoni, Endingen (CH)

(73) Assignees: KONINKLIJKE PHILIPS N.V., AE Eindhoven (NL); PAUL SCHERRER INSTITUT, Villigen (CH)

( * ) Notice: Subject to any disclaimer, the term of this patent is extended or adjusted under 35 U.S.C. 154(b) by 112 days.

(21) Appl. No.: 16/614,064

(22) PCT Filed: May 14, 2018

(86) PCT No.: PCT/EP2018/062407
§ 371 (c)(1),
(2) Date: Nov. 15, 2019

(87) PCT Pub. No.: WO2018/210765
PCT Pub. Date: Nov. 22, 2018

(65) Prior Publication Data
US 2021/0153824 A1    May 27, 2021

(30) Foreign Application Priority Data
May 15, 2017 (EP) ...................................... 17171111

(51) Int. Cl.
*A61B 6/04* (2006.01)
*G01N 23/04* (2018.01)
(Continued)

(52) U.S. Cl.
CPC ............ *A61B 6/4291* (2013.01); *A61B 6/484* (2013.01); *A61B 6/502* (2013.01); *G21K 1/067* (2013.01);
(Continued)

(58) Field of Classification Search
CPC ............. G02B 27/52; G21K 2207/005; G21K 2201/064; G21K 1/06; G21K 1/067;
(Continued)

(56) References Cited

U.S. PATENT DOCUMENTS

| 5,208,654 A | 5/1993 | Shao et al. |
| 5,291,539 A | 3/1994 | Thumann et al. |

(Continued)

FOREIGN PATENT DOCUMENTS

| JP | 2008-545981 A | 12/2008 |
| JP | 2012-013530 A | 1/2012 |

(Continued)

OTHER PUBLICATIONS

International Search Report dated Jul. 30, 2019 for PCT/EP2018/062407.
(Continued)

*Primary Examiner* — Irakli Kiknadze
(74) *Attorney, Agent, or Firm* — Hunton Andrews Kurth LLP

(57) ABSTRACT

An exemplary mounting structure can be provided for interferometric imaging and an interferometric imaging apparatus comprising same. The mounting structure comprises at least one curved surface for receiving an interferometric grating to rest thereon. The surface can be provided having a plurality of apertures, whereas that the grating when so received, covers at least one of the apertures.

15 Claims, 4 Drawing Sheets

(51) Int. Cl.
*G21K 1/06* (2006.01)
*A61B 6/00* (2006.01)

(52) U.S. Cl.
CPC ...... *A61B 6/0414* (2013.01); *G21K 2201/064* (2013.01)

(58) Field of Classification Search
CPC ............. G21K 1/062; G21K 2201/061; G21K 2201/067; G21K 1/10; G21K 1/02; G21K 1/065; G21K 2201/06; G21K 7/00; A61B 6/484; A61B 6/4291; A61B 6/4035; A61B 6/4233; A61B 6/06; A61B 6/4464; A61B 6/502; A61B 6/00; A61B 6/032; A61B 6/4007; A61B 6/4092; A61B 6/4241; A61B 6/482; A61B 6/5205; A61B 6/585; A61B 6/587; A61B 6/0414; A61B 8/00; A61B 8/4488; A61B 8/12; A61B 8/4494; A61B 8/5207; A61B 8/54; A61B 6/4266; A61B 6/4435; A61B 6/508; A61B 6/0407; A61B 17/1757; A61B 5/055; A61B 90/06; A61B 2034/2048; A61B 2090/374; A61B 6/037; A61B 6/4417; A61B 90/11; A61B 90/17; A61B 10/0233; A61B 17/70; A61B 2017/90; A61B 34/10; A61B 6/022; A61B 6/035; A61B 6/04; A61B 6/0487; A61B 6/12; A61B 6/40; A61B 6/42; A61B 6/4208; A61B 6/4028; A61B 6/4441; A61B 6/466; A61B 6/481; A61B 6/504; A61B 6/08; A61B 6/547; A61B 6/5282; G01N 23/041; G01N 23/20075; G01N 2223/1016; G01N 2223/204; G01N 2223/313; G01N 2223/401; G01N 2223/423; G01N 2291/02475; G01N 23/02; G01N 29/0654; G01N 29/262; G01N 29/46; G01N 21/47; G01N 21/8806; G01N 21/956; G01N 2201/06146; G01N 2201/0631; G01N 2201/0638; G01N 2201/0686; G01N 2291/015; G01N 2291/0422; G01N 2291/0423; G01N 23/046; G01N 23/201; G01N 2223/303; G01N 2223/3301; G01N 2223/3302; G01N 2223/3306; G01N 2223/419; H01J 2235/086; H01J 35/08; H01J 2235/062; H01J 2235/068; H01J 35/025; H01J 35/116; H01J 2235/1291; H01J 2235/18; H01J 35/112; H01J 35/12; H01J 2235/088; H01J 2235/1204; H01J 35/10; H01J 35/101; H01J 35/108; G01S 15/89; G01S 15/8915; G01S 15/8997; G01S 17/90; G01S 7/52025; G01S 7/52039; G01S 7/52046; G01S 15/8927; G01S 15/8977; G01S 7/52047; H05G 2/003; H05G 2/005; H05G 2/008; G10K 11/32; G10K 11/341; G10K 11/346; G06T 2207/10116; G06T 5/002
USPC ........................................ 378/37, 62, 84, 85
See application file for complete search history.

(56) References Cited

U.S. PATENT DOCUMENTS

| | | | |
|---|---|---|---|
| 5,357,553 | A | 10/1994 | Ferlic et al. |
| 2004/0202279 | A1 | 10/2004 | Besson et al. |
| 2005/0175154 | A1 | 8/2005 | Kondradason et al. |
| 2012/0002785 | A1 | 1/2012 | Kaneko |
| 2012/0099705 | A1* | 4/2012 | Murakoshi ........... A61B 6/4291 378/85 |
| 2012/0134472 | A1 | 5/2012 | Kaneko |
| 2013/0010926 | A1* | 1/2013 | Tada .................... A61B 6/4291 378/62 |
| 2013/0259194 | A1 | 10/2013 | Yip et al. |
| 2014/0177789 | A1 | 6/2014 | Baturin et al. |
| 2015/0023465 | A1* | 1/2015 | Sato ................. G01N 23/20075 378/36 |
| 2015/0151527 | A1* | 6/2015 | Teshima ................ B32B 27/306 378/36 |
| 2016/0135769 | A1 | 5/2016 | Wang et al. |

FOREIGN PATENT DOCUMENTS

| | | |
|---|---|---|
| RU | 2545319 C2 | 3/2015 |
| WO | 2006131235 A1 | 12/2006 |
| WO | 20120125086 A1 | 9/2012 |
| WO | 2015090949 A1 | 6/2015 |
| WO | 20160177903 A1 | 11/2016 |
| WO | 2017055181 A1 | 4/2017 |

OTHER PUBLICATIONS

Written Opinion of the International Searching Authority dated Jul. 30, 2019 for PCT/EP2018/062407.
Extended European Search Report dated Dec. 1, 2017 issued for European Application No. 17171111.2.
Koehler, Thomas et al., "Slit-Scanning differential X-ray phase-contrast mammography: proof-of-concept experimental studies" Medical Physics, The International Journal of Medical Physics Research and Practice, vol. 42, No. 4, pp. 1959-1965, Apr. 2015.
Russian Office Action dated Mar. 12, 2021 for Russian Patent Application No. 2019137989 and English Translation.
Notice of Reasons for Refusal for Japanese Patent Application No. 2019-563146 dated Oct. 5, 2021 (English language machine translation enclosed).

* cited by examiner

GRID-MOUNTING DEVICE FOR SLIT-SCAN DIFFERENTIAL PHASE CONTRAST IMAGING

CROSS REFERENCE TO RELATED APPLICATION(S)

This application relates to, and claims the benefit and priority from International Patent Application No. PCT/EP2018/062407 filed on May 14, 2018 that published as International Patent Publication No. WO 2018/210765 on Nov. 22, 2018, which claims the benefit and priority from European Patent Application No. 17171111.2 filed on May 15, 2017, the entire disclosures of which are incorporated herein by reference in their entireties.

FIELD OF THE DISCLOSURE

The invention relates to a mounting structure, to an interferometric assembly, to an interferometric imaging apparatus and to a method for manufacturing an interferometric assembly.

BACKGROUND INFORMATION

Mammography is a promising application area of grating-based differential phase-contrast imaging and dark-field imaging. However, geometrical constraints in this area are relatively strict. Two of these geometrical requirements are the desire for a very short interferometer (in the order of a few centimeters) and a short overall system length (source-detector distance) of the imaging apparatus.

However, a short interferometer requires very finely pitched gratings and therefore high aspect ratios. When these gratings are chosen to be planar, a substantial visibility reduction for off-axis rays is observed in systems with a short total length due to oblique incidence. As reported in Koehler et al in "Slit Scanning Differential X-Ray Phase-Contrast Mammography: Proof-of-Concept Experimental Studies", Medical Physics, 42(4), April 2015, the visibility at the outermost detector lines is only half the visibility of the central detector line.

To address at least some of the above, curved interferometers have been designed in order to ensure that the visibility remains high all over the detector area.

However, it has been observed that image quality in such imaging systems, especially of those of the scanning type, are sometimes sub-optimal.

SUMMARY OF EXEMPLARY EMBODIMENTS

There may therefore be a need to address at least some of the above noted shortcomings.

One of the objects of the present disclosure is to address such deficiencies, and can be solved by the subject matter of various exemplary embodiments of the present disclosure as described herein. It should be noted that the following described aspect of the present disclosure equally applies to an interferometric assembly, an interferometric imaging apparatus and a method of manufacturing the interferometric assembly.

Accordingly, a mounting structure can be provided for interferometric imaging according to an exemplary embodiment of the present disclosure. Such exemplary structure can comprise at least one curved surface for receiving an interferometric grating to rest thereon. The surface can have a plurality of apertures, and the grating, when so received, covers at least one of said apertures. In one exemplary embodiment, the apertures are arranged to be alignable, when assembled in an imaging apparatus, with detector pixels on a detector.

The exemplary mounting structure can facilitate safe, accurate, and robust mounting of curved gratings so as to focus same towards the focal spot of an X-ray imaging system in which they are to be used. The curved support surface can have apertures (e.g., slits or others) in order to foster an undisturbed passage of X-radiation through the exemplary mounting structure.

According to another exemplary embodiment of the present disclosure, the grating(s) resting on the curved surface can be supported, e.g., at a center region of the grating to avoid sagging, flexure, or other deforming of the mounted grating. A defined curvature can thus be provided and/or guaranteed. For example, the surface portions between the slits can provide a stable resting surface for the grating to better combat a possible grating deformation. The grating can remain focused even during the scanning operations of the imager in which it can be mounted.

Additionally and/or alternatively, according to yet another exemplary embodiment of the present disclosure, the robustness of the processing of detector signals can be maintained because relative motion between two gratings is substantially avoided. For example, grating deformations, such as those incurred during motion in scanning systems, can be one exemplary reason why the image quality can sometimes be sub-optimal. These grating deformations can disturb accurate signal processing of interference pattern caused by the interferometric gratings. The exemplary mounting structure can facilitate a secure mounting of curved interferometers, thus increasing the robustness of the signal processing, which can address the corrupting of quality/fidelity of the imagery in interferometric imaging, specifically in absorption imaging, phase contrast imaging, and dark-field imaging.

According to a still another exemplary embodiment of the present disclosure, the exemplary mounting structure can have apertures which are arranged to be alignable in projective registry with the detector pixels. Due to such exemplary configuration, when a divergent beam is used, the disturbance caused by edges of the slits or apertures of the mounting support can be kept low.

By using the configuration of the grating covering the apertures, there would be an inter-aperture portion of the support that acts to maintain the shape of the grating. Additionally, the aperture (e.g., pattern) can increase the rigidity of the curved support surface yet provide an even better definition of the corresponding curvature of the grating mounted thereto. The apertures can give rise to a complementary system of inter-aperture portions in the support surface. With respect to the grid covers the system of apertures and hence the inter-aperture portions, a stable support can be provided for the grating.

By utilizing the curved mounting plates, as provided in one exemplary embodiment of the present disclosure, it is possible to facilitate easy mounting in particular of gratings that are not pre-bent into curved shapes. This can be advantageous when tuning two or more gratings mounted on the structure in order to adjust the interference pattern, and also to ensure sufficient numbers of fringes across the detector.

According to yet another exemplary embodiment of the present disclosure, the mounting structure can comprise at least one retaining member configured to retain the grating on the curved surface in a curvature conforming to that of the curved surface. This can facilitate the grating to be curved according to the focusing parameters of the beam.

According to yet another exemplary embodiment of the present disclosure, the mounting can include a second curved surface with a plurality of apertures, the second surface being arranged opposite the at least one, first, curved surface, and the second curved surface being configured to receive a second interferometric grating. This can facilitate multiple gratings to be supported and held at fixed distance.

According to yet another exemplary embodiment of the present disclosure, the mounting structure can have the first and second curved surfaces are arranged to hold the respective interferometric gratings at a multiple of a Talbot distance.

According to yet another exemplary embodiment of the present disclosure, the mounting structure can be provided substantially in the shape of a cuboid having the at least one curved surface.

According to yet another exemplary embodiment of the present disclosure, the mounting structure can include a hollow space bounded on one side by the at least one curved surface. This can provided an advantage that, e.g., only the surfaces can contribute to disturbance of the beam.

In another exemplary embodiment of the present disclosure, a detector can be provided for interferometric imaging which can comprise radiation sensitive detector pixels, and the radiation sensitive detector pixels can be arranged in a pattern. Such pattern can be alignable, when assembled in an imaging apparatus, with apertures present in a mounting structure for an interferometric grating. This can facilitate providing the detector which is adapted to an advantageously constructed interferometer.

In yet another exemplary embodiment of the present disclosure, an assembly can be provided that can comprise the exemplary mounting structure(s) according to various exemplary embodiments described herein. Such exemplary assembly can also include a detector for interferometric imaging comprising radiation sensitive detector pixels being arranged in a pattern. The exemplary pattern can be alignable, when assembled in an imaging apparatus, with apertures present in a mounting structure for an interferometric grating. This can be advantageous by providing the detector which is adapted to an advantageously constructed interferometer.

According to a further exemplary embodiment of the present disclosure, an interferometric assembly can be provided which can comprise the exemplary mounting structure(s) according to various exemplary embodiments described herein, with the interferometric grating(s) mounted thereon. Such exemplary grating can be curved to conform to the curved surface of the mounting structure.

In yet a further exemplary embodiment of the present disclosure, the interferometric assembly can comprises the exemplary mounting plate(s) which can have a curvature that corresponds to that of the curved surface. The grating can be sandwiched between the curved surface and the mounting plate. This exemplary configuration can hold the grating securely in place.

According to yet another exemplary embodiment of the present disclosure, an interferometric imaging apparatus can be provided which can comprise an X-ray source having a focal spot and the exemplary interferometric assembly according to various exemplary embodiments described herein, in which the curved grating can be focused to the focal spot.

In another exemplary embodiment of the present disclosure, the exemplary interferometric imaging apparatus can comprise an X-ray detector, and the exemplary interferometric assembly can be arranged on or at least opposite to the detector.

According to a further exemplary embodiment of the present disclosure, the exemplary interferometric imaging apparatus can have the detector which includes a plurality of radiation sensitive detector pixels arranged in discrete groups of pixels. For example, the apertures of the mounting structure can be in registry with the groups of pixels.

In another exemplary embodiment of the present disclosure, the exemplary interferometric imaging apparatus can be a scanning apparatus and/or a mammography imaging apparatus.

The aspects described above and further aspects, features and advantages of the present disclosure may also be found in the exemplary embodiments which are described in the following with reference to the appended drawings and claims.

BRIEF DESCRIPTION OF THE DRAWINGS

Further exemplary embodiments of the present disclosure are detailed in the description of the Figures, where this description shall not limit the scope of the present disclosure and the drawings are not necessarily provided to scale. The Figures show.

Figure 1:
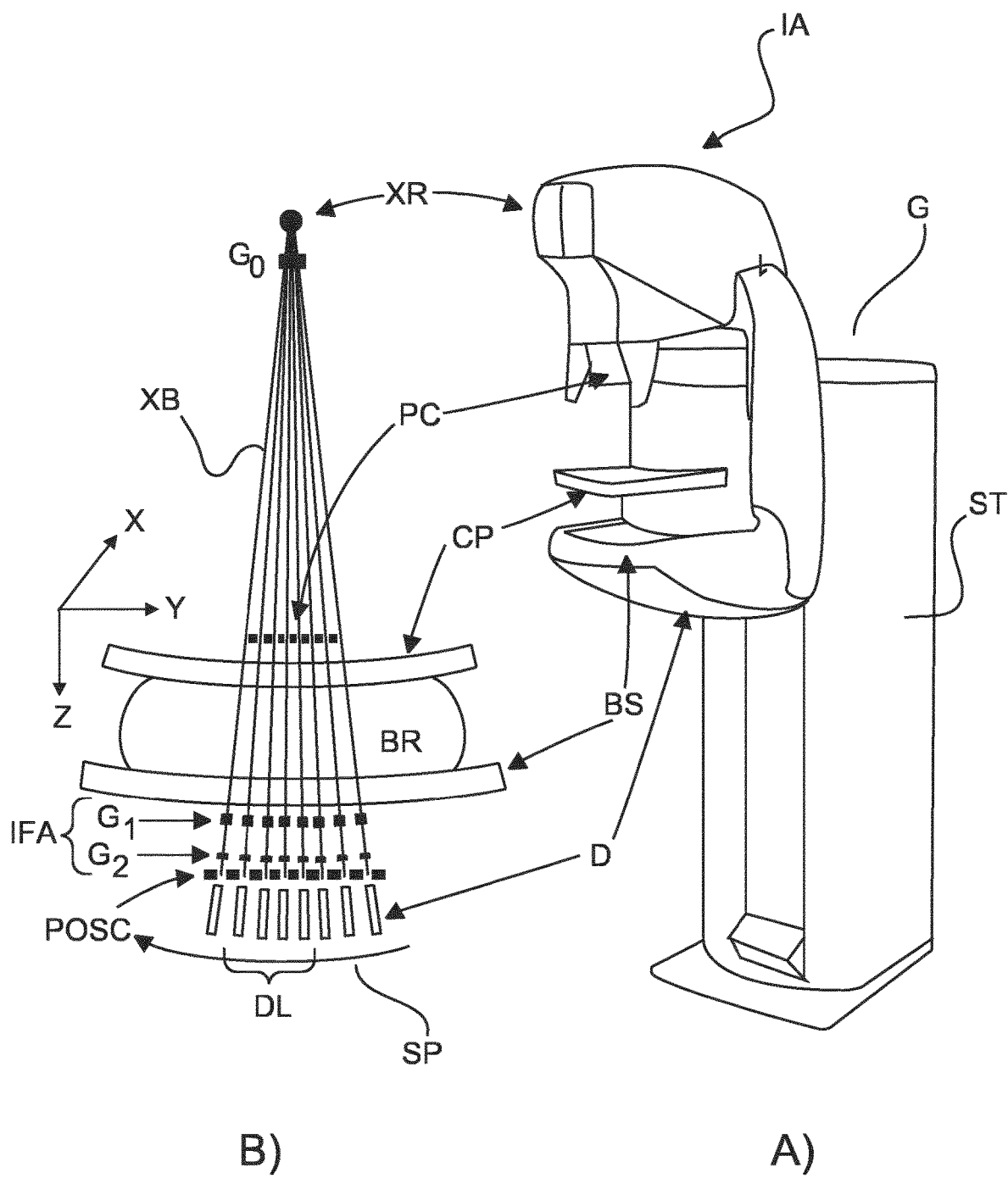
FIG. 1 is a diagram providing exemplary components on an X-ray imaging apparatus with an interferometer according to an exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure as defined by the appended claims.

DETAILED DESCRIPTION OF EXEMPLARY EMBODIMENTS

Exemplary embodiments of a mounting structure are described herein for at least one interferometric grating, e.g., for the purposes of interferometric X-ray imaging, as well as for others.

FIG. 1 schematically illustrates an X-ray apparatus IA equipped and configured for interferometric imaging having a mounting structure. For example, FIG. 1 shows two views, i.e., view A being a perspective view on the imaging apparatus IA with its housing and view B which illustrates a cut away frontal view in a schematic manner providing some components of the interferometric imaging apparatus IA. Although the description below references a mammography slit scanning system, such description is not limiting, as other interferometric imagers not necessarily in the field of mammography or not necessarily of the slit scanning type are also envisaged herein according to exemplary embodiments of the present disclosure.

As provided in view A of FIG. 1, the mammography X-ray imaging apparatus comprises a stand ST which is either floor or ceiling mounted or mobile as the case may be. FIG. 1 illustrates a floor mounted stand ST on which a frame G is mounted.

The frame G includes an X-ray source XR for emitting an X-ray radiation beam and opposite the source and provided across an imaging or examination region, an X-ray detector D for detecting said radiation.

As shown in FIG. 1, the X-ray radiation passes through the examination region in which the object of interest (e.g., the human breast BR) is placed during imaging. In more detail and with reference to view B of FIG. 1, the breast BR rests on a breast support BS and is compressed by an application of a compression plate CP to achieve a homogeneous and small breast thickness during imaging.

In an exemplary operation, the X-ray beam can interact with matter of the breast BR. The interaction can modify the X-ray beam and it is such modified beam that can be registered at an X-ray sensitive surface of the detector D. The X-radiation surface comprises a plurality of detector pixels.

The detector D can be a digital detector, such as, e.g., a flat panel scanner in full view or—a likely herein—a multi-line detector with discretely placed detector lines each comprised of individual detector pixels. The detector pixels can be operative to convert impinging X-radiation into electrical signals which are converted into projection imagery. In one exemplary layout, the detector lines can be non-continuous but are arranged in linear arrangement with gaps in between any two detector lines to form a series of detector lines (although other exemplary layouts are within the exemplary embodiments). For example, a plurality (e.g., 2-30 or more) of such series can be provided that can run parallel to each other, not necessarily equidistantly. For example, the series can be staggered so that the gaps in neighboring series are not in registry. The distance between two adjacent detector lines can be in general larger (e.g., by many order or magnitudes) than the pixel size or inter-pixel distance. While the later (pixel size or distance there between) can usually be in the μm range, it is also possible that they may be in the mm or even cm range. In view B of FIG. 1, the detector lines are shown as extending into the plane of the drawing so the view is along the detector lines.

Other detector pixel layouts are also envisaged to form different patterns. Indeed, discrete pixel groupings other than linear are also envisaged in alternative exemplary embodiments. For example, detector pixels may be arranged across the detector surface in discrete circular, elliptic, or polygonal (e.g. triangular, rectangular, etc.) groupings.

Optionally, there can be relative to the imaged object in the exam region, a pre-collimator PC, arranged between the object BR and the X-ray source, and also optionally a post collimator POST arranged between the detector D and the object BR can be provided.

The pre-collimator PC can divide via an aperture mask the X-ray beam generated at the X-ray source into a plurality of partial beams, such as fan beams. The fan beams shown in view A of FIG. 1 extend into the image plane. The individual fan beams can then pass through the imaged object BR and interact with an interferometric arrangement or assembly IFA (explained in more detail below). The post collimator can then operate to remove scatter contributions incurred during passage through the breast material and the fan beams now encoding absorptive, refractive, and small-angle scatter-type information experienced via the interaction with the breast tissue are then impinging on the radiation sensitive surface of the detector.

In the exemplary embodiment shown in FIG. 1 and described herein, the imaging apparatus is of the scanning type. In other words, while the imager IA can operate to acquire projection imagery of the object, there may be a relative motion between the object BR and the detector. This can be achieved in one exemplary embodiment by arranging the detector on a moveable scan arm (not shown) moveable relative to the breast BR. The detector can thereby be advanced along a linear or arcuate scan path SP post the breast from underneath.

Other exemplary embodiments in the non-medical or non-mammographic arts are can be provided, where the detector D remains stationery whilst it is the object that is scanned past the detector. In yet other exemplary embodiments, the X-ray beam can be deflected electrostatically to so effect the scanning whilst the source XR or detector D remain stationary. In other exemplary embodiments, the detector can be stationery, and the X-ray source traces out the path. Alternatively, both detector and X-ray source can be scanned past the object.

In summary, and no matter the envisaged scanning implementations used in the interferometric imager IA, the projection imagery can be acquired along different projection directions whilst a motion between the X-ray beam and at least a part of the X-ray interferometer is affected. In the case of mammography, the projection direction can be similar or the same. In the case of tomosynthesis, this direction may change. The scanning operation can be useful when the detector lines have the above described gaps.

According to a further exemplary embodiment of the present disclosure, co-ordinate system X,Y,Z and related nomenclature can be provided and shown in view B of FIG. 1. Axis Y indicates the direction of the scanning. Perpendicular thereto and extending into the drawing of FIG. 1, is axis X which is parallel to the direction of the detector lines. Lastly, axis Z designates the main propagation direction of the primary beam, more particularly, indicates the direction of the optical axis of the imaging apparatus IA. Spatio-relational terms such as "in front of", "below", "above", "downstream/upstream" etc. are taken along the optical axis in the propagation direction of the X-ray beam. Additionally, description herein provides spatio-relational terms such as "distal" and "proximal" which are understood to refer to the relative position or location with respect to the detector. More specifically, the qualifier "proximal" can indicate a closer position relative to the detector (surface) than a distal position/location.

With respect to the interferometric aspect of the exemplary apparatus according to the exemplary embodiments of the present disclosure, this facilitates imaging not merely for absorptive properties of the imaged matter, and also for refraction or small scattering phenomena experienced by the X-ray beam in its passage through matter of the imaged object BR. The imaging for refractive properties can be referred to as phase contrast imaging and this term shall be used herein although this is not to exclude the imaging for the other related properties, attenuation, and small-angle scattering. Similarly, contrast generated by small-angle scattering can often be called dark-field contrast.

The exemplary interferometric arrangement IFA facilitates extracting any of these three properties, such as absorption, refraction, and small-angle-scattering. The exemplary interferometric arrangement can include an interferometer and at least a part of this exemplary interferometer can be mounted on the mounting device (which is discussed in more detail herein). In the exemplary embodiment as shown in FIG. 1, the exemplary interferometer can be formed of two interferometric gratings G1 and G2. The exemplary interferometric arrangement IFA can be mounted in one (but not all embodiments) opposite the detector D's X-ray sensitive surface, e.g., is mounted between the breast BR and the detector D. In particular, the interferometric arrangement IFA is mounted onto the detector D to effectively cover the detector D's X-ray sensitive surface.

G1 shown in view of B of FIG. 1 is a phase grating and G2 is an absorber grating. Each of the gratings $G_1$ and $G_2$ comprises an alternate series of parallel grating lines processed (e.g. by etching, cutting, or other techniques) into the surface of a (possible but not necessarily) flexible substrate. This substrate is—in one exemplary embodiment—a flexible, i.e. thin, silicon wafer but other variants are also envisaged such as a polyimide film (e.g., Kapton™) or graphite or other. The grating lines define a series of trenches separated by respective ridges. This exemplary system of ridges and trenches run preferably along the detector lines along X, perpendicular to the scan direction Y and other directions such as along the scan direction Y are also within the scope of the present disclosure.

In order to achieve the necessary field of view there is typically not only a single grating $G_1$ or $G_2$, but there is a respective series of these gratings arranged in series along direction X so as to tile the gratings over the detector's X-ray sensitive surface. For example, in one exemplary embodiment, there two, three or more of these grating can be arranged side by side. Similar series of analyzer gratings $G_2$ can be arranged opposite the phase grating(s). Below, a reference is made to "grating $G_1$" or "grating $G_2$", with the understanding that these terms may refer to respective series of such gratings. Unless a micro-focus tube is used, a source grating $G_0$ can be provided (which can also be or include an absorber grating) arranged at or close to the X-ray source to make the emitted X-ray beam at least partially coherent.

It is not necessary in all exemplary embodiments for the grating to include two gratings $G_1$ and $G_2$, and also the source grating $G_0$ is not necessary if the source XR used is capable of producing natively coherent X-ray beam. In particular, exemplary embodiments can be provided where the interferometer IF comprises only a single grating $G_1$ whilst the function of the analyzer grating is performed by the detector having suitably spaced detector pixels and lines.

The exemplary interferometric arrangement shown FIG. 1 is merely one exemplary embodiment. For example, a reversed grating geometry can also be envisaged, where the phase grating $G_1$ can be arranged on the same side as the source grating before the object to be imaged and it is only the grating $G_2$ that is arranged below the imaged objects.

The one or more gratings $G_1$ (in the following $G_1$ will be referred of the issues as a generic reference to any one of the three gratings $G_1$, $G_2$ or $G_0$), as the case may be.

The function of the interferometer can be to produce an interference pattern detectable at the detector. This exemplary interference pattern can then be analyzed by suitable signal algorithms or procedures as explained elsewhere from which the three quantities attenuation image, phase contrast image, and dark field image can be computed, on which more below.

Each of the gratings can be defined by a quantity, called the pitch, which refers to the distance between any two of the mentioned walls in the grating lines. These walls extend in the direction of the optical axis to confer a certain height along Z axis. This exemplary height relative to half of the pitch (or width of the trenches) is referred to as the aspect ratio. Depending on the wavelength of the X-ray source used a specific pitch must be chosen in order for the grating to perform its interferometric imaging functionality.

This functionality for the exemplary interferometer IF (of Lau-Talbot type) can be as follows. The phase grating diffracts the incoming fan beams into an interference pattern and this is re-produced at precisely defined distances downstream of the phase grating due to the Talbot effect at so-called Talbot distances of different orders or—in the case of a phase grating $G_1$—the phase modulation can be transformed into an intensity modulation at so-called fractional Talbot distances, which are also often called just Talbot distances. The Talbot distance can be a function of the pitch of the phase grating and the wavelength of the X-ray radiation. At one of these Talbot distances (e.g., the $1^{st}$ order, to achieve compact built along the Z axis), the analyzer grating $G_2$ is located in one exemplary embodiment. Interferometric phase contrast imaging can rest on the observation, that this exemplary interference pattern can be disturbed if the object BR (to be imaged) is introduced into the examination region. In other words, one first records an interference pattern without there being an object present in the examination region. This can be sometimes referred to as air scan. When the object is introduced into the examination region and exposed to the X-ray beam, a different interference pattern can be produced by phase grating and this different interference pattern can be introduced as a perturbed version of the interference scan as per the air scan. This exemplary disturbance is likely caused by a refractive and small angle scattering actions caused by the matter in the image object.

Because of the presence of the analyzer grating $G_2$, this disturbance can be translated into an intensity modulation by incurring a relative motion within the interferometer and the X-ray beam. In traditional methods, this is performed by phase stepping where one of the gratings is moved relative to the others. (See, e.g., F. Pfeiffer et al. in "Phase retrieval and differential phase-contrast imaging with low-brilliance X-ray sources," Nat. Phys. 2, 258-261 (2006)). However, this type of phase stepping as in Pfeiffer et al is not envisaged herein. Instead, according to the exemplary embodiment of the present disclosure, the gratings can be fixedly arranged opposite each other with no relative motion between the two gratings. Instead, the scanning motion is used to induce this intensity pattern. A sinusoidal signal model can be fitted to this intensity pattern produced by co-operation between the two gratings. This has been reported elsewhere, e.g., in the publication by Koehler et al.

The exemplary interferometric arrangement IFA can further include, e.g., a mounting structure MS on which one or two of the gratings $G_1$ is mounted.

Figure 2:
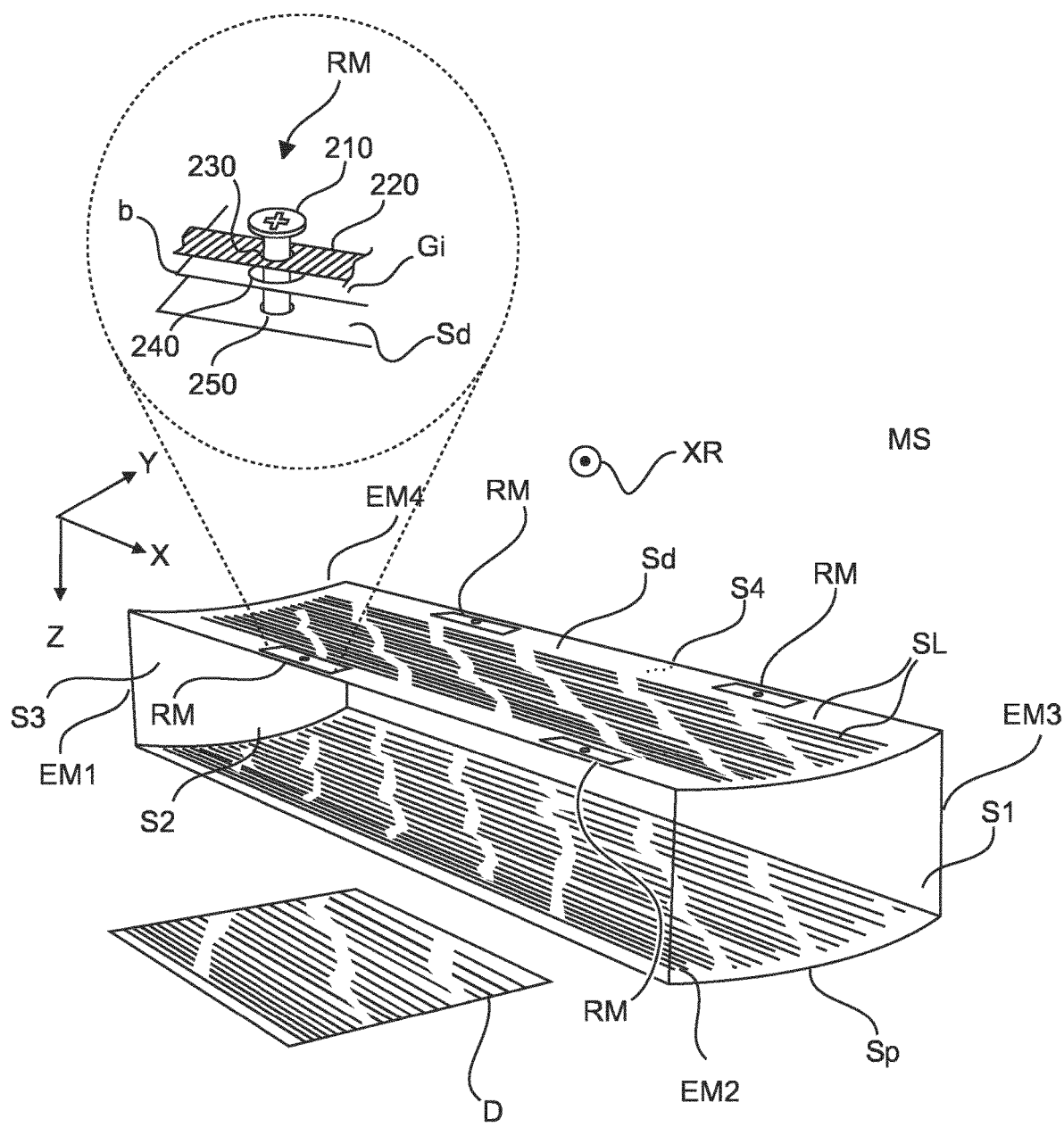
FIG. 2 is a diagram of a mounting structure for at least one interferometric grating according to an exemplary embodiment of the present disclosure.

FIG. 2 shows a perspective view of the mounting structure MS according to an exemplary embodiment of the present disclosure. Only a portion of the detector surface D is shown in FIG. 2 under the grating mount MS. Thus, a footprint of the mounting structure MS can be substantially coextensive with the radiation sensitive surface of the detector D.

Generally, the function of the mounting structure MS can be two-fold. First, the mounting structure can facilitate holding two gratings at the required Talbot distance from each other in case of $G_1$ and $G_2$ (there can also be a functional requirement—likewise dependent from pitch and wavelength—for the distance at which $G_0$ and $G_1$ should be apart). A height along the Z axis of the mounting structure MS can thus equal essentially to a Talbot distance of desired order (e.g., of 1st order). Second, the mounting structure MS can be configured to facilitate a curved arrangement of the gratings $G_1$ in order to focus the gratings $G_1$ towards the X-ray source XR. This facilitates an increasing visibility as otherwise shadowing effects occur for gratings away from the optical axis Z. More particularly, the ridges of the gratings can be angled progressively away from the optical axis such that imaginary planes that pass though respective ridges intersect in a line (e.g., referred to herein as the "focal axis") through the focal spot of the X-ray source.

Generally, the mounting structure can be or include a frame comprising two curved surfaces, e.g., a distal support surface St and a proximal support surface $S_p$.

In one exemplary embodiment and as shown in FIG. 1, the mounting device MS can be mounted above the detector surface. Each of the support surfaces can be configured to receive respective one of one or two of the gratings $G_1$. For instance, in one exemplary embodiment the distal surface is to receive one or more phase grating (tiles) $G_1$ while the opposed proximal surface $S_p$ can be to receive one or more analyzer gratings (tiles) $G_2$.

In inverse geometry the distal surface Sd receives the source grating $G_0$ whilst the proximal one $S_p$ receives the phase grating $G_1$. As described herein, the area of the individual gratings is in general smaller than the support surfaces $S_p$, $S_d$. The surfaces $S_d$ and $S_p$ are hence respectively tiled by a series of such gratings. For example, according to an exemplary embodiment, the distal surface can receive a series of three phase grating tiles and correspondingly the proximal surface receives a series of three analyzer grating tiles, while these numbers are purely exemplary and depend on the relative sizes of the surfaces $S_p$, $S_d$, and the gratings $G_1$.

The exemplary grating support surfaces $S_d$ and $S_p$ are curved in the same sense or direction as shown in FIG. 2 to support focusing the gratings Gi that rest thereon. In other words, the support surfaces $S_d$ and $S_p$ are each cylindrical surfaces of imaginary concentric cylinders having their longitudinal axes coinciding with the focal axis passing through the focal spot FS. For example, a profile of each of the curved surfaces can have a single extremal point. For illustrative purposes, as shown in FIG. 2 (and also in FIG. 3 to be discussed herein) the bending radius (i.e., the radii of the cylinders) are shown smaller (~150 mm) than the exemplary order of curvature, which in one exemplary embodiment is in the order of 50-70 cm, e.g., about 65-66 cm, and in a further example, about 660 mm. These exemplary radii can correspond to the distance between detector D and focal spot FS and is a convenient size in particular for mammographic applications. Applications other than mammographic may call for different curvatures.

The mounting structure MS has in general as its envelope or outer shape a cuboid with one pair of its edges (e.g., the pair of long edges) extending along the detector lines, that is along the X axis. The curved grating support surfaces $S_p$, $S_d$ resemble roof shingles upside down thus conferring to the mounting box the general shape of a "curved cuboid".

Tangential planes at the respective extremal points of the two curved support surfaces $S_p$, $S_d$ can be approximately perpendicular to the optical axis of the imager when the mounting structure MS is arranged in the imager IA. Four side portions S1-S4 (being oriented essentially parallel to the optical axis) can be provided which can extend between the two curved support surfaces $S_p$, $S_d$.

The grating mounting MS can be in general hollow so the two surfaces $S_p$, $S_d$ and the side portions S1-S4 enclose or outline a hollow space HS although this does not necessarily exclude structures or other stabilizing elements that are run in the inside of the mounting structure MS across the hollow space HS. This (quasi-)hollow construction can facilitate essentially undisturbed passage of the X-ray beam(s) through the mounting structure MS. As shown in FIG. 1, the side portions are merely indicated by their location but are themselves cutaway to admit visualization of the hollow HS space enclosed by the mounting "box" MS.

The four side portions S1-S4 can be either closed or likewise comprises one or more openings to save weight and material. For example, at least one (e.g., all) of the side portions S1-S4 can be of essentially massive construction (that is, have no or few through-holes). These side portions then form 4 walls connecting the two surfaces $S_p$, $S_d$, in which case the mounting structure MS is more akin to a box. However, this is not to exclude other exemplary embodiments where, one or more, or all side portions include one or more openings, the mounting structure MS thus being more akin to a truss work structure or the kind. One extreme embodiment of this is where the side portions S1-S4 "degenerate" into four straight edge members EM1-EM4 connecting respective corners of the two opposing surfaces $S_p$, $S_d$ and extending substantially perpendicular therefrom. In such exemplary embodiment, the mounting structure is more akin to a cuboid frame.

In order to further reduce disturbance of the X-ray beams that pass through the mounting structure MS at least one, but preferably both, of the curved support surfaces $S_d$ and $S_p$ have a respective pattern of apertures SL formed therein. In those exemplary embodiments where one of the surfaces $S_p$, $S_d$ bears no aperture pattern, this surface should then be formed from an X-ray translucent material. If the apertureless surface is the proximal one for receiving the phase grating G1 its material should be "structure-less" at the spatial scale of the pitch of G1 so as not to disturb the interference. The apertures may have the form of slits in the case where the detector pixels are grouped in lines. However, for both the apertures and the detector pixel groups, other arrangements are possible.

Thus, an exemplary mounting structure for interferometric imaging can be provided, which comprises at least one curved surface for receiving an interferometric grating to rest thereon. The surface can have a plurality of apertures and the grating when so received, covers at least one of the apertures. The apertures can be arranged to be alignable, when assembled in an imaging apparatus, with detector pixels on a detector.

The exemplary mounting structure allows safe, accurate, and robust mounting of curved gratings so as to focus same towards the focal spot of an X-ray imaging system in which they are to be used. The curved support surface has apertures such as slits or others in order to foster un-disturbed passage of X-radiation through the mounting structure.

For example, the grating(s) resting on the curved surface can be supported in particularly at a center region of the grating to avoid sagging, flexure, or other deforming of the mounted grating. A defined curvature can thus be guaranteed. In particular, the surface portions in between the slits provide a stable resting surface for the grating to better combat grating deformation. The grating can remain focused even during scanning operations of the imager in which it is mounted.

Likewise, the robustness of the processing of detector signals can be maintained because relative motion between two gratings can be substantially avoided. For example, grating deformations, such as those incurred during motion in scanning systems, can be one reason why the image quality is sometimes sub-optimal. These grating deformations disturb accurate signal processing of interference pattern caused by the interferometric gratings. The exemplary mounting structure facilitates secure mounting of curved interferometers, thus increasing the robustness of said signal processing and hence corrupting quality/fidelity of the imagery in interferometric imaging, specifically in absorption imaging, phase contrast imaging, and dark-field imaging.

In one exemplary embodiment of the present disclosure, the apertures are a pattern of linear slits. In this exemplary embodiment, the slit pattern can conform to the layout of the detector lines which are likewise interrupted and slightly offset to each other. In other words, the slot pattern cut into or otherwise formed into each of the curved surfaces comprises a series of discrete slits extending along the detector line direction (along the X axis shown in FIG. 1) with interruptions and each of the slit series is staggered relative to the adjacent ones. This exemplary arrangement defines a series of diagonally slit free portions or bands that run linearly across the curved surfaces $S_d$, $S_p$, as shown in FIG. 2. These bands of "inter-aperture" portions provide a distributed, stable support for the gratings to avoid flexure or sag or other deformation even during scan motion, thus ensuring at all times during the imaging operation essentially constant, well-defined grating curvature. The advantage of this exemplary arrangement can be that reduced disturbance of the X-ray beams is achieved at least for those X-ray beams that will eventually land on a detector pixel.

In general, the trenches and ridges of the gratings $G_i$ (in particular of $G_1$ and $G_2$) are run in parallel to the course of the slits. In view B of FIG. 1B, the furrow/ridges extend into the plane or the drawing along axis X.

Such exemplary slit pattern is merely an exemplary embodiment for an aperture layout. For example, the aperture pattern formed in the curved support surfaces can in general correspond to the layout of the groupings of the detector pixels in the detector surface. In the exemplary embodiment where the detector lines, i.e., lines of detector pixels, are continuous (that is, have no gaps), the aperture pattern may be accordingly formed as a series of parallel, continuous slits.

In one exemplary embodiment, the dimensions and shape of the slits correspond to the dimensions (length and thickness) and shape of the fan beams into which the native beam has been divided by the pre-collimator PC.

In general, the system of apertures in the support surface(s) $S_p$, $S_d$ defines a trellis work or a (cross) grid structure in said surface $S_p$, $S_d$, with the apertures having shapes such as curved (e.g., ellipse or circular), or rectangular, lozenge shaped etc., depending on the shape of the detector pixel groupings. The exemplary layout pattern of the apertures as formed in the surfaces $S_p$, $S_d$ can be such that the complementary layout pattern of inter-aperture portions (i.e., the parts of the surface where there are no apertures) can be in registry with those portions of the detector surface located between the groups of pixels to avoid disturbing the X-ray beam(s).

It can be important to form the apertures large enough to avoid interference effects on their own. In fact, as a variant to the exemplary embodiment shown in FIG. 2, the shape of the apertures not necessarily conforms (tightly) with the shape of the partial beams. The apertures may be formed substantially larger and/or may have a different shape than the pre-collimated partial beams. In one exemplary embodiment of the present disclosure, exactly two apertures defined by a single connecting member (e.g., strut or strip) can be provided that runs in X or Y direction to connect opposing edges of the respective surface $S_p$, $S_d$. In addition and according to an alternative embodiment, a second connecting member may run across the first connecting member to so define 4 (e.g. rectangular) apertures. In other words, in this exemplary embodiment the surface "degenerates" to a border portion connected by the one or two connecting members. Therefore, as used herein, the relation of "being in registry" between the detector pixel groupings and the aperture pattern does not necessarily imply correspondence in shape and size of the groupings versus the apertures although this is indeed the exemplary embodiment shown in FIGS. 1 and 2 (as discussed further herein).

The exemplary groupings and the aperture pattern should merely be so aligned that for each (partial) beam that passes through any given aperture there is a detector pixel grouping that lies in the path of that beam. Such exemplary spatial registry between detector pixel groupings and aperture pattern extends to the aperture mask of the pre-collimator PC. Additionally, the respective aperture pattern of the two support surfaces $S_p$, $S_d$ are also in registry to each other. It will also be understood, that in some exemplary embodiments, the partial beams into which the native beam is divided, can be in general divergent. In other words, the projection is not necessarily a parallel one, and may also be a central/perspective one. The registry relationship between the support surface patterns, the pre-collimator and the location of the detector pixel groupings can therefore be understood to be configured to respect this and may therefore be called more generally a relation of "projective registry", that is, the aperture patterns and the detector pixel grouping are in registry under the applicable projection to be used in the imaging geometry of the imaging apparatus IA. It can be beneficial to size the apertures or slits slightly wider than the actual detector pixel groupings to allow for tolerances in the mechanical alignment, beam creation and mounting support manufacture.

Herein above, the detector D has been described as having pixels arranged in discontinuous lines. However, as previously described, other exemplary arrangements of the pixels are possible. Furthermore, it can be advantageous to define a slit pattern in the mounting structure MS according to the characteristics of the grating or following mechanical constraints. For example, certain exemplary arrangements of slits can offer greater mechanical stability. In this exemplary situation, it can be advantageous to arrange the pattern of the pixels on the detector D to be in registry with the slit pattern of the mounting structure MS. Thus, the detector (D) for interferometric imaging can comprise radiation sensitive detector pixels, the radiation sensitive detector pixels being arranged in a pattern, in which the exemplary pattern is alignable, when assembled in an imaging apparatus, with apertures present in a mounting structure for an interferometric grating.

An exemplary advantage of adapting the mounting structure MS to the detector D is that it may be possible to use detectors with existing arrangements of pixels i.e. it may avoid changing the detector.

Due to the exemplary mounting structure MS being hollow, each of the curved support surfaces has an outside face and an inside face. In one exemplary embodiment of the present disclosure, it is possible to mount the respective gratings to the outside faces of the two curved support surfaces $S_p$, $S_d$. In other exemplary embodiments, both of the gratings or both grating series $G_1$, $G_2$ can be mounted to the respective inside faces of the curved surfaces $S_p$, $S_d$. Mixed arrangements are also are within the scope of the present disclosure, e.g., where one of the gratings or series is mounted on the outside face whilst the other series is mounted on the inside face of the curved surface. More specifically, in one exemplary embodiment, the phase grating $G_1$ or a series thereof is mounted on the outside face of the distal curved surface SD whilst the analyzer grating series $G_2$ is mounted on the inside surface of the inside face of the curved second support surface SP. In the previously discussed exemplary embodiments, the source grating $G_0$ is preferably (but not necessarily in all exemplary embodiments) likewise curved and mounted on a similar mounting structure MS located between the X-ray source and the object BR. The mounting structure for the source grating $G_0$ can have a single curved or flat support surface. In inverse geometry, the analyzer grating $G_2$ can be solely mounted on a separate mounting structure MS (preferably with a single curved surface) between object OB and detector D, whilst phase grating $G_1$ and source grating $G_0$ are mounted together in the same structure, with $G_0$ on the distal surface and $G_1$ on the proximal one.

The gratings can either be pre-bent into a curved shape and are then mounted onto the curved surface $S_p$, $S_d$. Alternatively, the gratings can be initially plane and are then urged into the curved shape and into contact with the respective face of the curved surface $S_d$ or $S_p$. Specifically, in order to securely retain the gratings on the respective curved surfaces the mounting box MS comprises a plurality of retaining members RM broadly arranged along the edges of the respective curved surfaces $S_p$, $S_d$. As shown in FIG. 2, only the retaining members on the distal surface $S_d$ are shown. Only four are shown for illustration in FIG. 2. However, a similar arrangement of retaining members is also to be found on the opposite proximal surface $S_p$.

The inset of FIG. 2 shows additional details of the retaining member RM according to one exemplary embodiment, configured to achieve substantially uniform distribution of contact pressure. In one exemplary embodiment, the retaining member comprises engagement activation parts 210, such as bolts (the corresponding nuts are not shown) or screws and a rail member 220. In one exemplary embodiment, the grating $G_i$ comprises unprocessed border regions b. In other words, there are no grating lines in these border regions b. Holes 240 are arranged in these border portions b of the gratings $G_i$. These holes are substantially larger than the bore of the bolt 210. A second set of holes 230, smaller in diameter than the grating holes 240, are formed into the rail structure 220 and a third set of holes ISO is formed in the underlying surface $S_d$ or $S_p$ that is to receive the respective grating. The bolt 210 is passed first through the rail hole 230, then through the grating hole 240 and is then received in a hole 250 of the underlying curved surface $S_p$, $S_d$. Because the grating hole 240 is substantially larger than the bore and because of the overlaying rail, the bolt's head and bore never contact the grating $G_1$ directly. Instead, the bolt's head, upon introduction of the bolt into the reception hole 250, urges the rail member 220 into contact with the grating $G_i$ so that upon complete insertion of the bolt the unprocessed border portion b of the grating is securely sandwiched between the rail member and the underlying curved surface $S_p$, $S_d$. In one exemplary embodiment, each retaining member RM has its own rail member 220, or plural retaining members share one continuous common rail member. However, the retaining members in shown in FIG. 2 can be according to one exemplary embodiment among many exemplary embodiments described herein. For example, gratings $G_i$ may instead be glued, soldered or otherwise affixed in a manifold of different ways. As a further exemplary variant to the above exemplary embodiments, the grating(s) $G_i$ may not necessarily have the unprocessed border portion(s) b. Instead, the grating through-holes 240 may thus be formed in a processed area of the grating(s) $G_i$.

Although FIG. 2 refers to the distal support surface $S_d$, completely analogous retaining members can also be used for the inside or outside face of the proximal support surface SP. By ensuring that the retaining members' engagement activation parts 210 does not come into contact with the delicate gratings $G_i$, damage can be avoided and the contact pressure can be uniformly distributed along the border portions b of the grid $G_i$.

The retaining members RM can be preferably not arranged on the edge of the support surface $S_p$, $S_d$ that is proximal to the breast BR during imaging, and are instead arranged at two or more of the remaining three edges. In other words, the retaining members RM can be arranged on the edges of the respective support surface $S_p$, $S_d$ that run parallel to the underlying detector and perpendicular to the scan direction of the X-ray imager. One or more of the retaining members may also be arranged at the far edge (in the perspective view of the exemplary embodiment shown in FIG. 2) that extends in scan direction. Preferably, the retaining members are equidistantly spaced (e.g., every 10 mm) to engage the grating $G_i$ tiles. In one exemplary embodiment, two or more retaining members are used per edge for each of the grating tiles.

Figure 3:
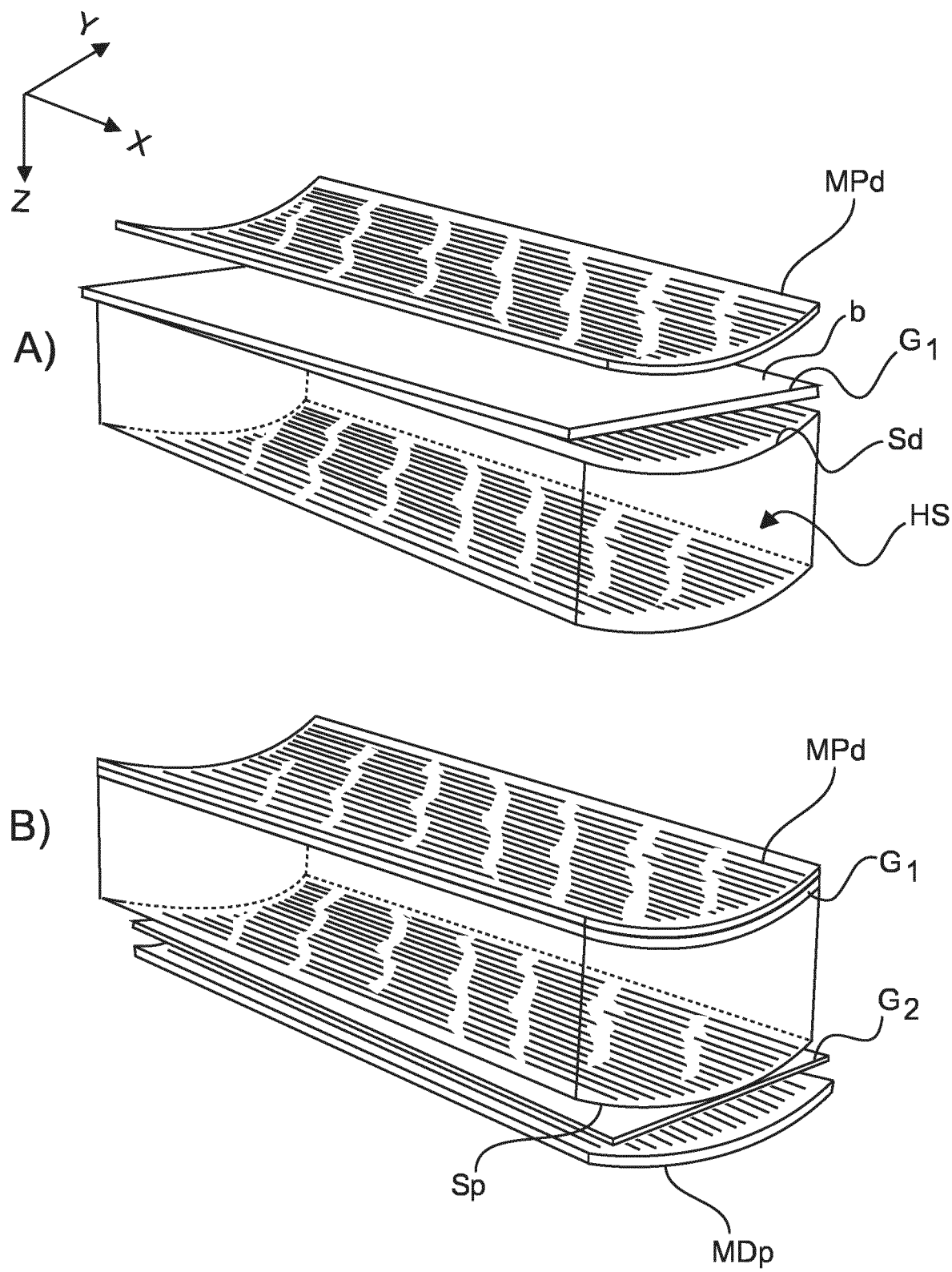
FIG. 3 is a diagram of the mounting structure for at least one interferometric grating according to another exemplary embodiment of the present disclosure.

FIG. 3, in views A and B thereof a further exemplary embodiment of the mounting structure MS including respective mounting plates MPd, MPp is shown, e.g., one for mounting on the distal support surface $S_d$ (shown in view A) and/or one (shown in view B) for mounting on the proximal surface $S_p$. It is not necessary to have two such mounting plates MPp,MPd as exemplary embodiments can be provided, where only one of the two support surfaces $S_p$, $S_d$ has such a plate MPd or a plate MPp.

The mounting plate MPp, MPd is likewise not flat, but instead curved having a curvature that corresponds to the curvature of the support surfaces $S_p$, $S_d$ on which it is mountable. When mounted, the respective grating $G_i$ is effectively sandwiched between the mounting plate MPd, MPp and the underlying support surface $S_p$, $S_d$. For example, the mounting plate can be pre-shaped to match the shape of the curved support surfaces $S_p$, $S_d$.

Having such pre-bent mounting plates MPd, MPd can be advantageous in the exemplary embodiment where the gratings $G_i$ themselves are not pre-bent into shape but are initially flat in a relaxed state. The gratings $G_i$ are assumed to possess sufficient flexibility to be deformable non-destructively into the desired curved shape conforming to the curvature of the surfaces $S_p$, $S_d$. The, initially, flat grating $G_i$ is then forced to assume a matching curved shape by pressure-applying the curved mounting plate MPd, MPd onto the grating toward the support surface $S_p$, $S_d$. The respective grating $G_i$ is urged by the mounting plate MPd, MPp into contact with its supports surface $S_p$, $S_d$. The bias of the grating against deformation is overcome whilst the mounting plate MPd, MPp is moved towards the support surface $S_p$, $S_d$ under application of force to deform the grating into the desired curved shape.

In one exemplary embodiment, the mounting plates MPd, MPp can be retained in this position after being so applied by similar retaining means RM as explained above in relation to the exemplary embodiment shown in FIG. 1. To this end, border portions of the mounting plates may therefore include corresponding holes for the bolts of the receiving means RM to pass there through. One or both of the mounting plates can include a respective aperture pattern (such as a slit pattern as shown in FIG. 2) to match the aperture pattern of the respective support surfaces $S_p$, $S_d$. Again, the respective slits in the mounting plates are in projective registry (in the same sense as explained above) to afford an essentially undisturbed passage of the plurality of beamlets there through. Because of the closeness of the mounting plate and its support surface $S_p$, $S_d$, it overlays, the two aperture patterns can be expected in general to be in registry under parallel projection, with the apertures being located under each other. Again, a correspondence in shape and size is not necessary but is preferable, as shown in the FIG. 2, for the illustrated exemplary embodiment. For example, it may be sufficient for present purposes for the apertures in the mounting plate MPp, MPd to be larger than the apertures $S_L$ formed in the underlying support surfaces $S_p$, $S_d$. The mounting plates MPp, MPd are not necessarily envisaged for permanent mounting as explained above but may be used instead as mere mounting tools to force the grating into shape and place onto the curved support surface $S_p$, $S_d$. After mounting, the gratings $G_i$ that are then secured, while the mounting plate MPd,MPp is removed thereafter. An exemplary embodiment of this will be described further below in connection with the exemplary method shown in FIG. 4. Likewise, for the mounting structure MS, when mounted opposite the detector, it is beneficial and import that the slits in the two surfaces $S_p$, $S_d$ and the slits or apertures in the mounting plates, if any, are all in registry with the layout of the detector pixels groups.

As described herein with the exemplary embodiments shown in FIGS. 2 and 3, rather than mounting the phase and analyzer gratings $G_1$ and $G_2$ opposite to each other onto the mounting structure MS (that is, $G_1$ distal and $G_2$ proximal) and by mounting the source grating onto a second such mounting structure, the inverse geometry can be used instead. In this inverse geometry, the source grating $G_0$ is mounted together with the phase grating $G_1$ onto the same mounting structure MS whilst the analyzer grating $G_2$ is mounted onto a separate such mounting structure. In particular, the source grating $G_0$ is mounted on the distal surface $S_d$ whilst the phase grating $G_1$ is mounted at the proximal surface $S_p$ of the same mounting structure.

As an alternative to the exemplary embodiment shown in FIG. 3, for $G_2$, the proximal mounting plate MPp does not necessarily feature aperture (slits). A sufficiently stiff and largely X-ray translucent material can also be used instead. This exemplary "aperture-less" option is in principle also available for the other mounting plate MPd for $G_1$ and care should be taken that the material used to force $G_1$ into its design shape does not negatively affect the interference-effects, i.e., the material should be "structure-less" at the spatial scale of the pitch of $G_1$.

The exemplary aperture pattern as applied to the support surfaces $S_p$, $S_d$ or to the mounting plate(s) MPp, MPd can be formed by laser cutting or other cutting or etching techniques.

An exemplary suitable material for the mounting structure MS is Invar steel (also known as FeNi36 or 64FeNi or derivatives thereof) or other alloys or any other suitably rigid material such as aluminum.

In one exemplary embodiment, the whole mounting stricture MS can be formed monolithically as a single block or box by cutting, milling, 3D-printing, etc., or by other forms of material processing.

In other exemplary embodiments, the mounting structure MS is integrally formed or assembled from different, distinct parts. For instance, the side walls (if any) S1-S4 are separately joined or affixed to the two curved support surfaces $S_p$, $S_d$, likewise forming separate components. In one exemplary embodiment, the mounting structure box MS is formed from two pieces that are joined in a plane that runs approximately halfway and parallel in between the two support surfaces $S_p$, $S_d$ in FIG. 2. In other words, in this exemplary embodiment, the mounting structure is assembled from two cuboid halves, each comprising the respective curved support surface and each having respective parts of the side walls S1-S4 or at least the four side edges EM1-EM4 perpendicularly projecting therefrom. These two cuboid halves are then joined together at their respective side portions or S1-S4 or edges EM1-EM4 by screwing, gluing, bolting or otherwise in order to form the cuboid shape as shown in FIGS. 1 and 2.

It is also possible to make the mounting structure MS a multi-tiered structure, i.e., having an arrangement which defines more than two curved surfaces. This would be useful in the event that more than two gratings are needed in this part of the interferometer. A hollow structure for the mounting structure would be suitable for this.

Although in the above embodiments, reference has been made to the mounting structure to be a "box" or of cuboid shape (e.g., a cube, or non-cuboid as shown in FIGS. 1 and 2), other geometries are not excluded herein in alternative embodiments. For instance, in alternative embodiments, the mounting structure MS has a cylindrical shape. More generally, any other 3D shape is also envisaged as matter of principle and the outer shape of the mounting structure MS will ultimately depend on the space requirement(s) in the imager IA and/or on the shape of the detector surface on which the mounting structure is attached to.

In order to ensure safe mounting of the mounting structure onto the detector or onto any other relevant part of the imaging apparatus, a suitable adaptor piece can be interposed between the lower curved support surface $S_p$ and the surface of the detector housing which is in general plane. These adaptor pieces may comprise a curved portion that matches, and is configured to receive the curved support surface $S_p$, whilst an opposing edge of the adaptor piece thereto corresponds to the part of the equipment (such as the detector housing) of the imager IA to which it attaches to. In particular, this opposing edge may be straight to ensure safe footing on the planar surface of the detector.

Figure 4:
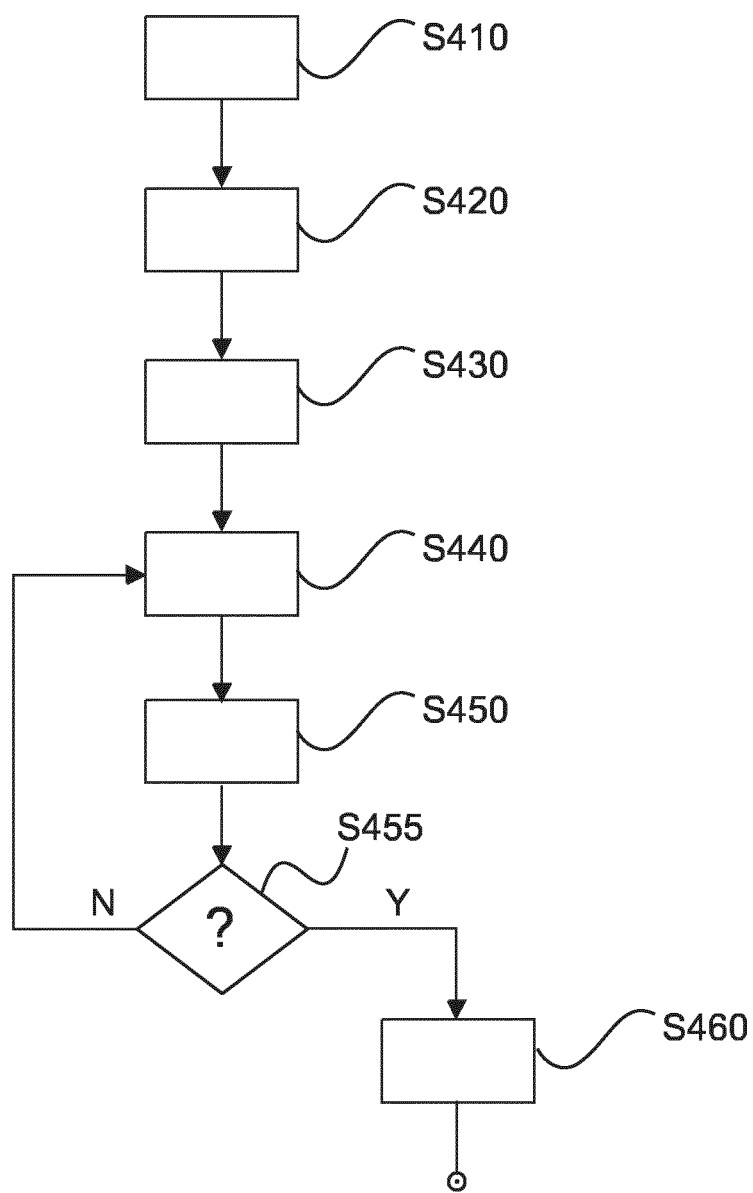
FIG. 4 is a flow diagram of a method for mounting gratings onto a mounting structure according to an exemplary embodiment of the present disclosure.

FIG. 4 which shows a flowchart of a method to manufacture an interferometric assembly according to an exemplary embodiment of the present disclosure. For example, the exemplary method can be for mounting the gratings onto a mounting structure MS with one or two curved support surfaces to respectively receive such gratings (as shown in the exemplary embodiments of FIG. 2 or 3).

The two grating structures $G_1$ and $G_2$ should be mounted relative to each other to ensure that the interference pattern has a sufficient number of periods extending across the detector lines. This is to ensure robustness of the signal processing that is applied to the detector signals when extracting the interferometric quantities, absorption, phase contrast and small angle scattering contributions as briefly mentioned above. In order to ensure that a sufficient number of interference fringes are achieved in this way, the gratings do not necessarily have to be parallel to each other due to slight imperfections in the manufacturing of the gratings.

For example, the trenches in the respective gratings may not necessarily be parallel to each other when mounted on the block MS. Rather, a slight twisting or other dislocation may be required or used to ensure the above mentioned sufficient number of interference fringes.

Turing now to the method in more detail, at step S410, the first of the two gratings (say $G_1$ or $G_2$) is applied to one of the curved surfaces of the mounting structure. This first grating is fixed securely to the surface $S_p$ or $S_d$ so that the grating is securely held there with the grating conforming to the curvature of the support surface and the mounting plate MP (if any).

In step S420, the second grating is now applied to the opposing support surface $S_p$ or $S_d$ of the mounting structure but is only provisionally applied thereto. Preferably but not necessarily, such second grating is $G_1$. For example, the second grating is urged into contact with its support surface, though it is not yet bent over but is allowed to remain flat at this stage merely touching the support surface in a line of contact with the curved support surface and, for now, is in contact only at said line of contact. In particular, the grating at this stage is still moveable relative to the fixed mounting grating at the opposite support surface. Yet more particularly, the second grating so provisionally mounted is tilt-able around a vertical axis Z that runs perpendicular through both support surfaces $S_p$ and $S_d$ and/or is tiltable about an axis that coincides with said line of contact.

The mounting structure with the two gratings affixed thereto is now exposed to X-radiation at step S430. This will now produce an interference pattern which is detected at a test detector, or preferably at a detector to be used in the imager IA in which the mounting structure is to be mounted. For example, the interference pattern can be visualized as test image on a monitor device.

This second moveable grating can be deliberately subjected to exploratory motion such as tilts, rotations and/or possibly shifts in step S440.

Concurrently thereto, at step S450, the interference pattern which is now changing due to the motion is observed as per the real time visualization on the monitor device. If the interference pattern is deemed satisfactory at step S455, that is, if there are enough interference fringes produced across the detector, the motion is ceased and the as yet moveable grating is then bent over to assume its final shape or position and is fixedly retained at step S460 to its support surface.

It will be appreciated that this exemplary method is particularly useful in cases where at least one of the grating is not pre-bent into a shape but is only forced into curved shape when mounted to the structure.

If the gratings are pre-bent into shape, the above method can still be applied, however, the test motions applied at step S430 can be somewhat restricted.

For the above described exemplary mounting method, the exemplary embodiment shown in FIG. 3 with the curved mounting plate MPp, MPd can be advantageous. The mounting plate MPd, MPd can provide a useful configuration to apply suitably distributed pressure onto the gratings to so force them into the curved shape and to ensure the grating securely rests against their respective curved surfaces Sp and Sd.

For example, for step S460, a micrometer arrangement can be used that facilitates to precisely tilt the provisionally attached second grating around the different axes to probe the resulting interference pattern. Specifically, the grating, in its flat, planar state, is held in a frame and this frame is tilt-able about one or more of the different axes by using different micrometer screws. Once the interference pattern is acceptable, a plunger, carrying the mounting plate MPp. MPd at one of its ends, is then forwarded through the frame, onto the grating which is then bent into curved shape against the support surface. Once the grating is in firm contact everywhere across its surface with the curved support surface $S_p$, $S_d$, the retainer members RM are engaged to secure the grating $G_i$ in shape and location to the mounting structure MS. The plunger then releases the mounting plate. The plunger then retires thus finishing the mounting operation. Alternatively, the mounting plate can be removed once the grating has been secured, the mounting plate thus merely serving as a mounting tool.

It should be understood that other ways of mounting the second grating may also be possible so to the use of the mounting plate as described above is not a necessity.

It should be appreciated that the above steps S455 and the exploratory motions in S430 provide an iterative method under visual guidance with interactive feedback. This can be achieved manually but may also be implemented on a computing unit suitably interfaced to a robotic platform to effect the exploratory motions. The interference pattern may be evaluated by an image processing algorithm whilst the exploratory motions may be computed based on data provided by random number generator (RNG) for instance. Other forms of automatizations are also envisaged herein.

It has to be noted that the exemplary embodiments of the present disclosure are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the exemplary embodiments of the present disclosure has been illustrated and described in detail in the drawings and foregoing description, such illustration and description are to be considered illustrative or exemplary and not restrictive. The present disclosure is not limited to the disclosed exemplary embodiments. Other variations to the disclosed exemplary embodiments can be understood and effected by those skilled in the art in practicing a claimed disclosure, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A mounting structure for interferometric imaging, comprising:
    at least one particular curved surface configured to receive a particular interferometric grating to rest thereon, the at least one particular curved surface having a plurality of apertures forming a grid,
    wherein the particular interferometric grating when received on the at least one curved surface, covers the plurality of apertures.

2. The mounting structure of claim 1, further comprising at least one retaining member configured to retain the first interferometric grating (Gi) on the at least one first curved surface in a curvature conforming to a curvature of the at least one first curved surface.

3. The mounting structure of claim 1, further comprising at least one further curved surface with a plurality of apertures, the at least one further surface arranged opposite the at least one curved surface, wherein the at least one particular curved surface is configured to receive a further interferometric grating.

4. The mounting structure of claim 3, wherein the particular and further curved surfaces are arranged to hold the particular and further interferometric gratings, respectively, at a multiple of a Talbot distance.

5. The mounting structure of claim 1, wherein the mounting structure is provided substantially in the shape of a cuboid having the at least one particular curved surface.

6. The mounting structure of claim 1, further comprising a hollow space bounded on one side by the at least one particular curved surface.

7. The assembly of claim 6, wherein the plurality of first apertures are arranged to be alignable in a projective registry with pixels of a detector.

8. An assembly comprising:
a mounting structure (MS) including at least one curved surface configured to receive an interferometric grating to rest thereon, the at least one curved surface having a plurality of apertures forming a grid, wherein the interferometric grating, when received on the at least one surface, covers the plurality of apertures; and
an interferometric imaging detector comprising radiation sensitive detector pixels which are arranged in a particular pattern, wherein the pattern is alignable, when assembled in an imaging apparatus, with the plurality of apertures present in the mounting structure.

9. An interferometric assembly, comprising:
a mounting structure including at least one curved surface configured to receive at least one interferometric grating to rest thereon, the at least one curved surface having a plurality of apertures forming a grid, wherein the at least one interferometric grating, when received on the at least one surface, covers the plurality of apertures, wherein the at least one interferometric grating is curved to conform to a curved surface of the mounting structure.

10. The interferometric assembly of claim 9, further comprising a mounting plate having a curvature that corresponds to a curvature of the curved surface, the at least one interferometric grating being sandwiched between the curved surface and the mounting plate.

11. An interferometric imaging apparatus, comprising:
an X-ray source having a focal spot; and
an interferometric assembly comprising a mounting structure including at least one curved surface configured to receive at least one interferometric curved grating to rest thereon, the at least one curved surface having a plurality of apertures forming a grid, wherein the at least one curved interferometric grating, when received on the at least one curved surface, covers the plurality of apertures, wherein the at least one curved interferometric grating is provided to be focused to the focal spot.

12. The interferometric imaging apparatus of claim 11, comprising an X-ray detector, wherein the interferometric assembly is arranged on or opposite to the X-ray detector.

13. The interferometric imaging apparatus of claim 12, wherein the X-ray detector includes a plurality of radiation sensitive detector pixels arranged in discrete groups of pixels, and wherein the plurality of apertures of the mounting structure are provided in registry with the discrete groups of pixels.

14. The interferometric imaging apparatus of claim 11, wherein the interferometric imaging apparatus is a scanning imaging apparatus.

15. The interferometric imaging apparatus of claim 11, wherein the interferometric imaging apparatus is a mammography imaging apparatus.

* * * * *